United States Patent
Marshall et al.

(10) Patent No.: US 7,174,515 B1
(45) Date of Patent: Feb. 6, 2007

(54) METHOD AND APPARATUS FOR INDEPENDENT DISPLAY IN A COMPUTER-AIDED DETECTION SYSTEM

(75) Inventors: Julian Marshall, Los Altos, CA (US); Jimmy Roehrig, Palo Alto, CA (US); Sandra J. Stapleton, Palo Alto, CA (US); John R. Johns, II, Sunnyvale, CA (US); Paul J. Fehrenbach, San Jose, CA (US)

(73) Assignee: R2 Technology, Inc., Santa Clara, CA (US)

( * ) Notice: Subject to any disclaimer, the term of this patent is extended or adjusted under 35 U.S.C. 154(b) by 231 days.

(21) Appl. No.: 09/992,046

(22) Filed: Nov. 21, 2001

(51) Int. Cl.
G06F 3/00 (2006.01)
A61B 8/00 (2006.01)

(52) U.S. Cl. .................. 715/763; 715/835; 600/437

(58) Field of Classification Search ................ 345/762, 345/763, 764, 835, 788, 173–182; 600/437, 600/509, 407; 382/128; 715/762–764, 835, 715/788
See application file for complete search history.

(56) References Cited

U.S. PATENT DOCUMENTS

| 5,828,774 | A | * | 10/1998 | Wang | .................... 382/128 |
|---|---|---|---|---|---|
| 5,917,292 | A | | 6/1999 | Marsanne | |
| 5,917,929 | A | * | 6/1999 | Marshall et al. | ............ 382/128 |
| 5,984,870 | A | * | 11/1999 | Giger et al. | ................ 600/443 |
| 6,014,452 | A | | 1/2000 | Zhang et al. | |
| 6,031,516 | A | | 2/2000 | Leiper | |
| 6,788,969 | B2 | * | 9/2004 | Dupree et al. | .............. 600/509 |
| 2002/0193676 | A1 | * | 12/2002 | Bodicker et al. | |
| 2003/0212327 | A1 | * | 11/2003 | Wang et al. | |
| 2004/0024303 | A1 | * | 2/2004 | Banks et al. | |

OTHER PUBLICATIONS

Wang, U.S. Appl. No. 60/252,946.*

* cited by examiner

Primary Examiner—Matthew Luu
(74) Attorney, Agent, or Firm—Blakely, Sokoloff, Taylor & Zafman, LLP; Judith A. Szepesi

(57) ABSTRACT

A method and apparatus for providing an independent display system for a computer aided detection (CAD) system that analyzes medical images. The independent display system comprises a screen to display a medical image including any marked regions of interest and a plurality of icons to interact with the screen. For one embodiment, the screen is a touch screen, such that the independent display system does not require a keyboard or cursor controller.

7 Claims, 17 Drawing Sheets

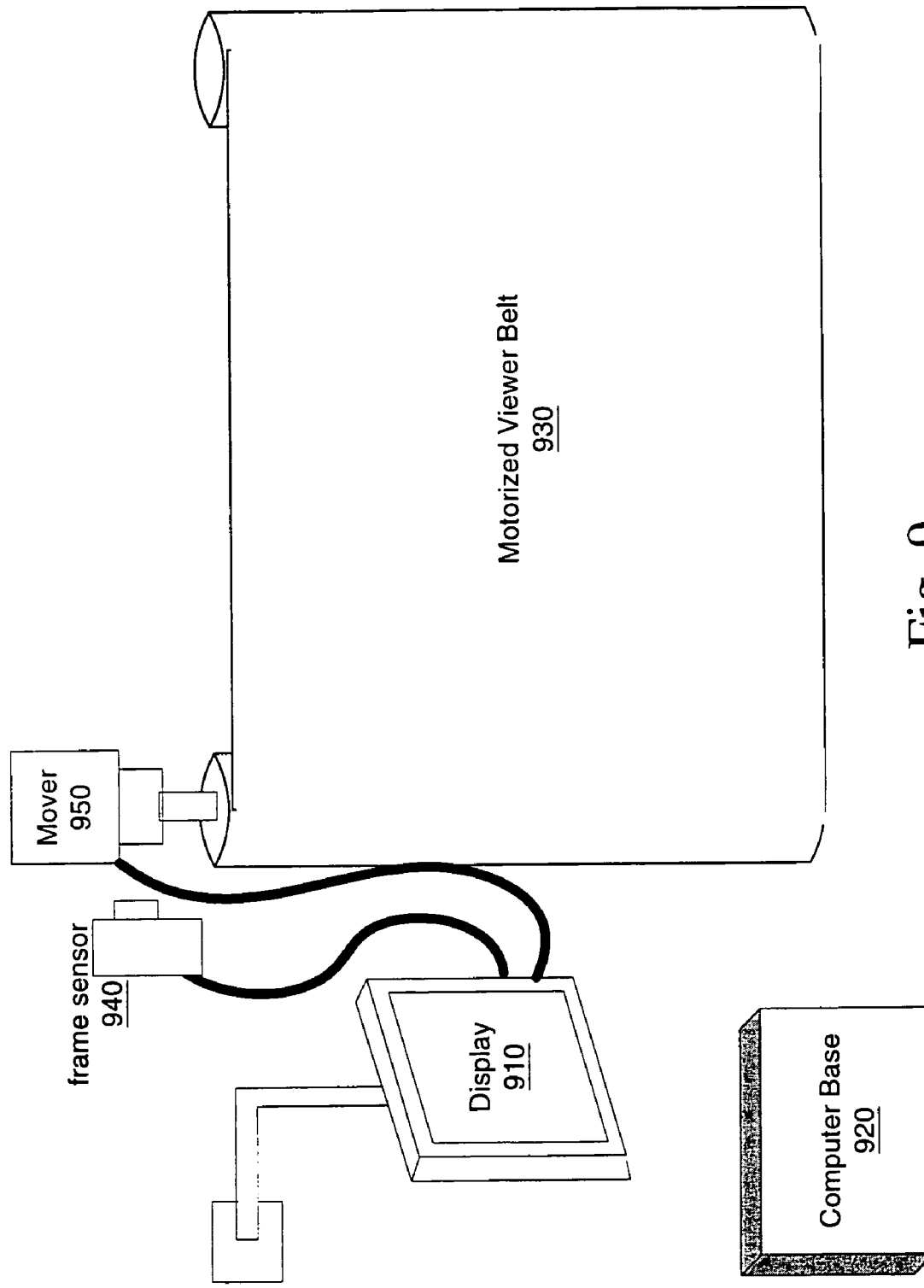

| LIGHTBOX ICON | #FRAMES | DESCRIPTION |
|---|---|---|
| | 4 | Lightboxes on either side of the Independent Display. Note that all four lightboxes can retain different Image ID assignments. |
| | 2 | Two lightboxes to the left and two to the right. Note that only the bottom two lightboxes can retain Image ID assignments. The upper 'X'ed lightboxes indicate priors and are not selectable. |
| | 3 | One lightbox to the left and two to the right. Note that all three lightboxes can retain Image ID assignments. |
| | 3 | Two lightboxes to the left and one to the right. Note that all three lightboxes can retain Image ID assignments. |
| | 2 | One lightbox to the left and one to the right. Note that both lightboxes can retain Image ID assignments. |
| | 1 | One lightbox to the left. Note that the lightbox can retain Image ID assignments. |
| | 1 | One lightbox to the right. Note that the lightbox can retain Image ID assignments. |
| None | 0 | Case selection is always accomplished with the barcode reader (or keyboard) |
| Design New Layout | N | User can create new layout, with lightboxes in the appropriate locations to mirror actual physical layout. |

Fig. 10A

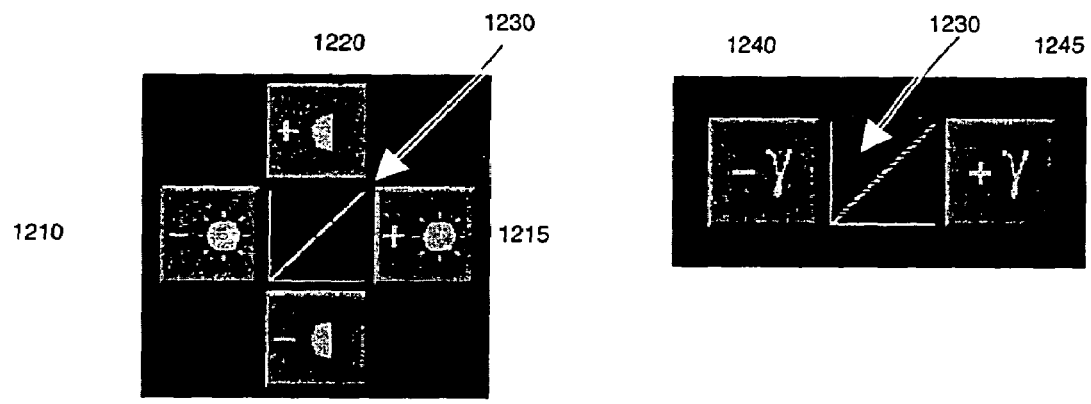
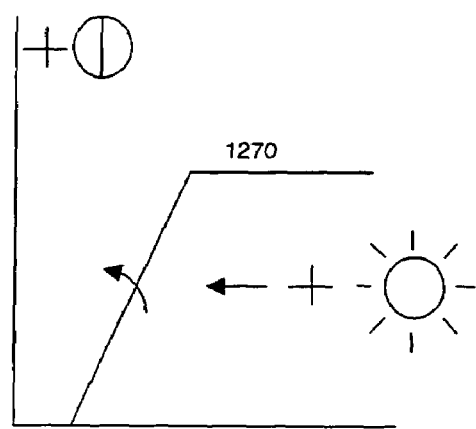
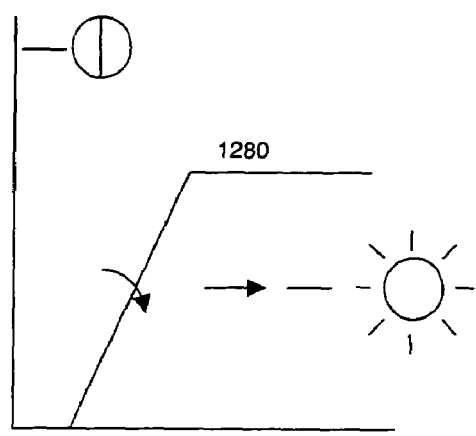
Fig. 12A
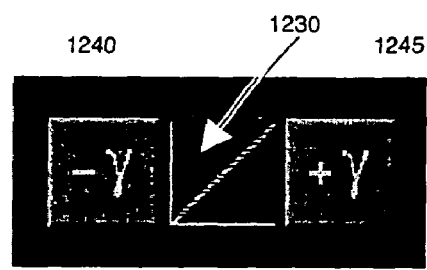
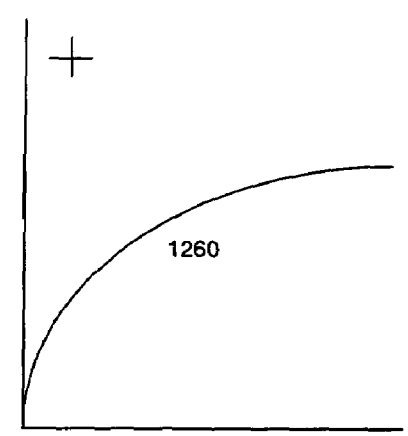
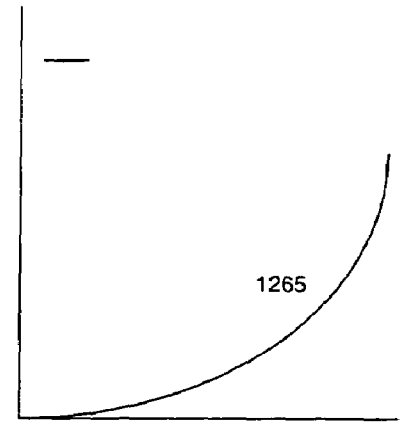
Fig. 12B

METHOD AND APPARATUS FOR INDEPENDENT DISPLAY IN A COMPUTER-AIDED DETECTION SYSTEM

FIELD OF THE INVENTION

The present invention relates to computer-aided detection (CAD), and more specifically, to an independent display to be used with a CAD system.

BACKGROUND

Computer-aided detection ("CAD") systems are used for the detection and identification of anatomic abnormalities in radiological images. In general, the radiological images are viewed in conjunction with annotated road maps of the locations and/or characteristics of suspected abnormalities found through computer processing of the radiological images. The annotated maps highlight and/or identify characteristics of suspected abnormalities to help the user better assess the presence and/or meaning and significance of abnormalities in the radiological images.

The detection of suspected abnormal anatomic regions in radiological images is done using a computer system with specialized software and specialized hardware. Such a system is known in the art. An example of such a system is described in U.S. Pat. No. 6,014,452 to Zhang.

In the prior art, CAD systems are used as follows. The radiological technician or the physician takes a set of radiological images of the patient following a preprogrammed protocol or procedure. A physician views the radiological images and reaches a preliminary diagnostic decision. The physician next views images and/or data generated by the CAD system. Each CAD processed image is a copy or a sub-sampled (with fewer pixels) copy of a radiological image, marked or annotated with a localized notation of the suspected abnormalities the CAD system has detected through computer analysis of a digitized version of the respective radiological image. After any reexamination of the areas of the radiological images that correspond to the positions of the suspected abnormalities displayed on the CAD system, the physician makes a final diagnostic decision.

The original radiological films are mounted on a conventional lightbox or a motorized lightbox for viewing. The annotated images of these mammograms are displayed on two small TV monitors located beneath the lightbox. Each small monitor displays two annotated images. Each annotated image comprises a sub-sampled digitized image of the respective film mammogram and locational markers marking the locations of the suspected abnormalities that the CAD processing detected.

The small monitors displaying the annotated images are integrated with the radiological image viewer, such as a motorized viewer. Thus, in order to review the images, the physician must invest in a special motorized viewer, which has an integrated CAD system image viewer, or must modify the existing viewer to incorporate the CAD monitors.

SUMMARY OF THE INVENTION

A method and apparatus for providing an independent display system for a computer aided detection (CAD) system that analyzes medical images. The independent display system comprises a screen to display a medical image including any marked regions of interest and a plurality of icons to interact with the screen. For one embodiment, the screen is a touch screen, such that the independent display system does not require a keyboard or cursor controller.

BRIEF DESCRIPTION OF THE DRAWINGS

The present invention is illustrated by way of example, and not by way of limitation, in the figures of the accompanying drawings and in which like reference numerals refer to similar elements and in which:

FIGS. 8 and 9 are embodiments of the setups of using an independent display system.

FIG. 10A is an illustration of one embodiment of various lightbox layouts and the corresponding icons.

FIGS. 12A and B are screenshots of embodiments of the display adjustment icons.

DETAILED DESCRIPTION

The present invention is an independent review station used to review medical images after computer aided detection (CAD) takes place. An independent review station is distinct from a standard review station, in that it is not incorporated into a viewer. For example, for mammograms, a viewer may be a motorized viewer, on which mammogram films are placed. The doctor reviews the images by moving the track to which the films are attached. However, the traditional motorized viewer does not have the ability to display digital images. The CAD output is digital image and/or data indicating regions of interest (ROIs). Since motorized viewers are a large investment, often costing in excess of $100,000, a doctor may not wish to replace the motorized viewer with a viewer that incorporates a digital display. The independent review station works with the traditional or existing viewer, and does not require any (modification of the viewer. The independent review station may be attached to a wall, attached to a moveable arm, or in some other way placed so the user may easily view the images displayed, without the independent review station being in the way.

Figure 1:
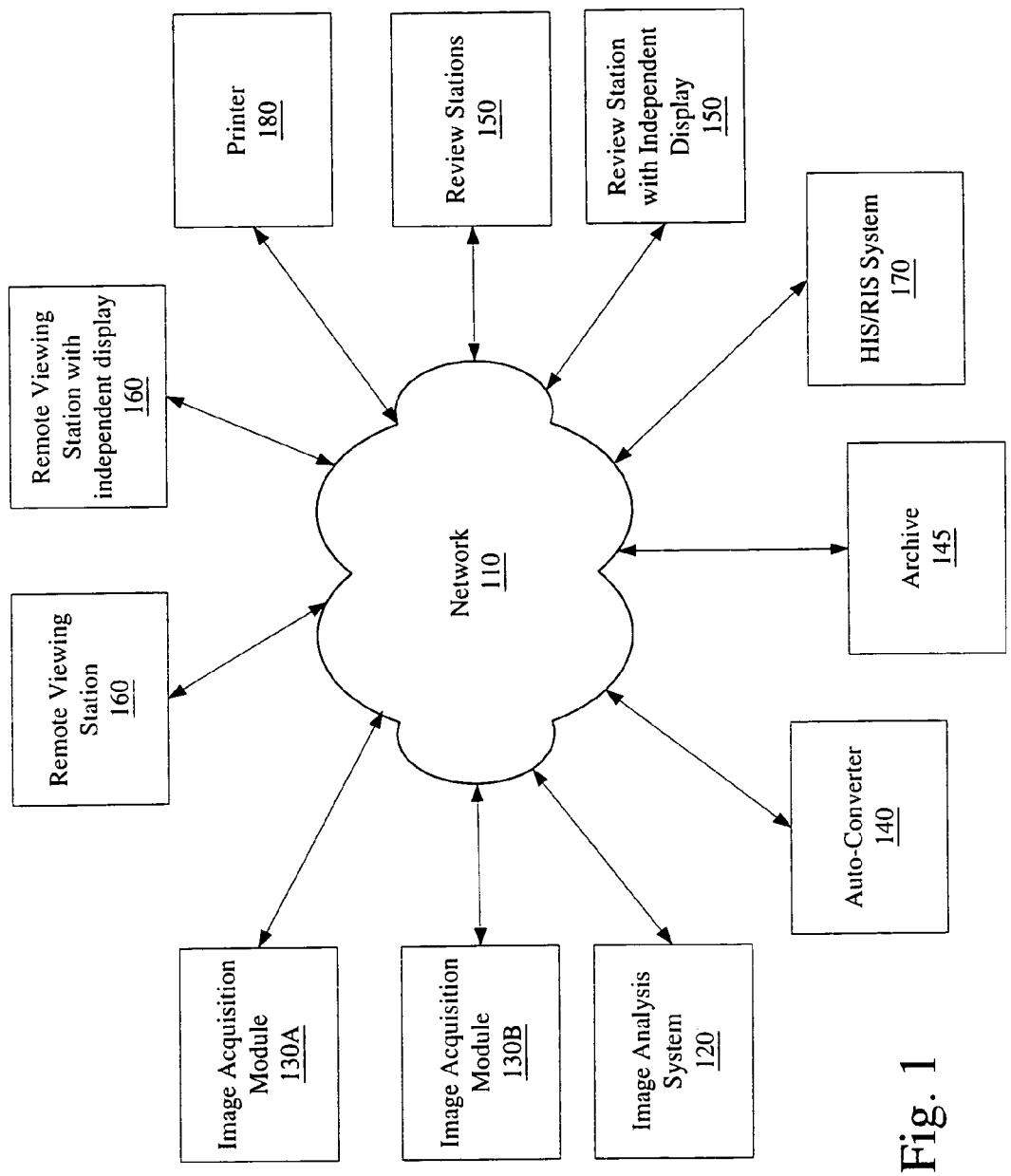
FIG. 1 is a block diagram of one embodiment of a network in which the present invention may be implemented.

FIG. 1 is a block diagram of a network that may be used with the present invention. The system includes one or more image acquisition modules 130A, 130B. The image acquisition modules 130A, 130B may be conventional medical image acquisition systems, which are known in the art, and/or digital image acquisition systems. Standard methods—such as mammogram films, CAT scans, chest X-rays, or others—may be used to obtain the analog or digital images, whether two or three-dimensional. The outputs of the image acquisition modules 130A, 130B, are digital or analog images.

These images are passed to image analysis system 120. For one embodiment, the images are sent through network 110 to image analysis system 120. Network 110 may be an internal local area network (LAN), a wide area network (WAN), the Internet, or any other type of network. For one embodiment, if the network 110 is not a local internal network, then the images sent by image acquisition modules 130A, 130B are encrypted or in some other way protected to ensure the patient's privacy. This permits the use of a centralized image analysis system 120 which may receive images from multiple offices that may be located anywhere in the world. Similarly, the analyzed images/output may be sent to review stations 150, 160 anywhere in the world.

The image analysis system 120 performs the preprocessing, recognition, and/or post-processing of the images. Exemplary image acquisition systems 120 that may be used for this are described in U.S. Pat. No. 5,828,774 to Wang, and co-pending application Ser. No. 09/992,059, by Roehrig et al. entitled "A Method And Apparatus For An Improved Computer Aided Diagnosis System."

The HIS/RIS (hospital information system/radiology information system) system 170 is coupled to the image analysis system 120, either directly or through network 110. The HIS/RIS system 170 provides patient information, in one of a variety of formats. Patient information may include patient data identifying the patient, as well as patient historical data, providing relevant historical information. For one embodiment, the HIS/RIS system 170 may provide data in the HL7 format. Alternative formats may be used.

The images processed by image analysis system 120 may be stored within a patient record, in the DICOM format. Alternative standardized, non-standardized, or proprietary formats may be used to store the image data, with or without the patient information.

For one embodiment, copies of the processed images are stored in system archive 145, such that at a later time, the previous images may be retrieved. For one embodiment, auto-converter 140 converts the images to a DICOM format. For one embodiment, the auto-converter 140 further converts the image to a lower resolution image, which is stored. For one embodiment, the stored image does not include any tagging or other indicators added by image analysis system 120. For another embodiment, the owner of the system may set the preferences as to the images stored in system archive 145.

The images are displayed to a reviewer at review station 150. Review stations 150 may be directly coupled to image analysis system 120, or coupled through a network. Review stations 150 may be incorporated into a motorized viewer, as described in U.S. Pat. No. 5,917,292, to Marshall et al. Alternatively, a review station 150 may be an independent display. Such an independent display review station 150 is described in more detail below.

For one embodiment, the images may further be viewed at remote viewing stations 160. Remote viewing stations 160 may be conventional computer systems coupled to the network 110. For one embodiment, the remote viewing station 160 may also incorporate an independent display. The independent display may be part of the same computer system that is the remote viewing station 160, or may be a separate unit that is set next to the remote viewing station 160. Thus, the reviewer is able to see the medical images using remote viewing station 160, and is further able to see the annotated CAD images using the independent display.

Remote viewing stations 160 permit a doctor in a remote location to review the images, and may be used to allow the patient or others to review the images remotely. Thus, for example, a radiologist at a central location may initially review and analyze the images, and annotate them. Then, the images, and notation—or a report generated based on the images and notation—is sent to a remote system where the doctor can review the data with the client. The images, report, or other output may be sent to a printer 180. The printer 180, for one embodiment, may print to film, to permit conventional review of the enhanced images. For one embodiment, the printer 180 may print multiple images, for example, one set of original images, a set of enhanced images, and a set of enhanced images with markers indicating the abnormalities found by the image analysis system 120. The printer 180 may be coupled to the image analysis system 120 and/or the system archive 140 either directly or through network 110. As discussed above with respect to the review stations 150, 160, the printer 180 need not be in the same location as the image analysis system 120.

Of course, not all of these elements must be present in order to implement the present system. At its simplest, the system includes an image acquisition module 130A, an image analysis system 120, and a review station 150 that permits viewing of the images. These systems 120, 130A, 150 may be coupled directly, without the use of a network 110. At its most complex, the system may be a distributed system having image acquisition modules 130A, 130B at various remote locations, while a central archive 140 and one or more image analysis systems 120 are used to process the acquired images. Then, the images may be sent to various local or remote review stations 150, 160. Note that although the image analysis system 120 illustrated as once central device, it may be a distributed system.

Figure 2:
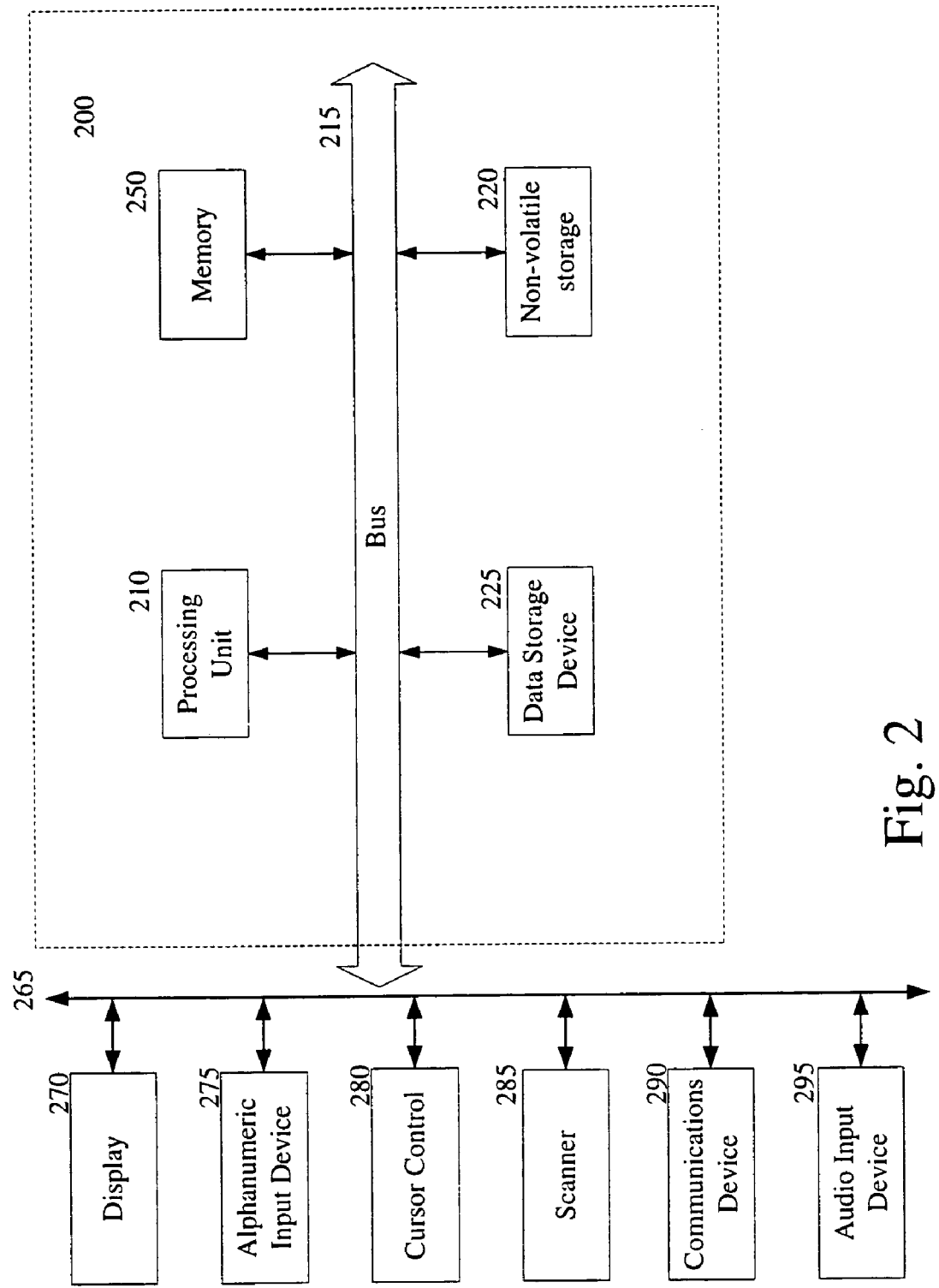
FIG. 2 is a block diagram of one embodiment of a computer system that may be used with the present invention.

FIG. 2 is one embodiment of computer system on which the present invention may be implemented. It will be apparent to those of ordinary skill in the art, however that other alternative systems of various system architectures may also be used.

The computer system illustrated in FIG. 2 includes a bus or other internal communication means 215 for communicating information, and a processor 210 coupled to the bus 215 for processing information. The system further comprises a random access memory (RAM) or other volatile storage device 250 (referred to as memory), coupled to bus 215 for storing information and instructions to be executed by processor 210. Main memory 250 also may be used for storing temporary variables or other intermediate information during execution of instructions by processor 210. The system also comprises a read only memory (ROM) and/or static storage device 220 coupled to bus 215 for storing static information and instructions for processor 210, and a data storage device 225 such as a magnetic disk or optical disk and its corresponding disk drive. Data storage device 225 is coupled to bus 215 for storing information and instructions.

The system may further be coupled to a display device 270, such as a cathode ray tube (CRT) or a liquid crystal display (LCD) coupled to bus 215 through bus 265 for displaying information to a computer user. An alphanumeric input device 275, including alphanumeric and other keys, may also be coupled to bus 215 through bus 265 for communicating information and command selections to processor 240. An additional user input device is cursor control device 280, such as a mouse, a trackball, stylus, or cursor direction keys coupled to bus 245 through bus 265 for communicating direction information command selections to processor 210, and for controlling cursor movement on display device 270. Additional input devices may include a scanner 285, to scan bar codes associated with images, and audio-input device 295, which receives verbal input from a user. Alternative input devices may also be implemented.

Another device that may optionally be coupled to computer system 200 is a communication device 290 for accessing other nodes of a distributed system via a network. The communication device 290 may include any of a number of commercially available networking peripheral devices such as those used for coupling to an Ethernet, token ring, Internet, or wide area network. Note that any or all of the components of this system illustrated in FIG. 2 and associated hardware may be used in various embodiments of the present invention.

For one embodiment, display 270, input device 275, and cursor control 280 may be combined into a single touch-screen. The touch screen display permits data entry using a touch sensitive screen.

It will be appreciated by those of ordinary skill in the art that any configuration of the system may be used for various purposes according to the particular implementation. The control logic or software implementing the present invention can be stored in main memory 220, mass storage device 225, or other storage medium locally or remotely accessible to processor 210. Other storage media may include floppy disks, memory cards, flash memory, or CD-ROM drives.

It will be apparent to those of ordinary skill in the art that the methods and processes described herein can be implemented as software stored in main memory 250 or read only memory 220 and executed by processor 210. This control logic or software may also be resident on an article of manufacture comprising a computer readable medium having computer readable program code embodied therein and being readable by the mass storage device 225 and for causing the processor 210 to operate in accordance with the methods and teachings herein.

The software of the present invention may also be embodied in a dedicated appliance containing a subset of the computer hardware components described above. For example, the dedicated appliance may be configured to contain only the bus 215, the processor 210, and memory 250 and/or 225, and a touch screen.

The device may also be configured to include a set of buttons or input signaling components with which a user may select from a set of available options. The dedicated appliance may also be configured to include an output apparatus such as a liquid crystal display (LCD) or display element matrix for displaying information to a user of the dedicated appliance. Conventional methods may be used to implement such a dedicated appliance. The implementation of the present invention for such a device would be apparent to one of ordinary skill in the art given the disclosure of the present invention as provided herein.

Figure 3:
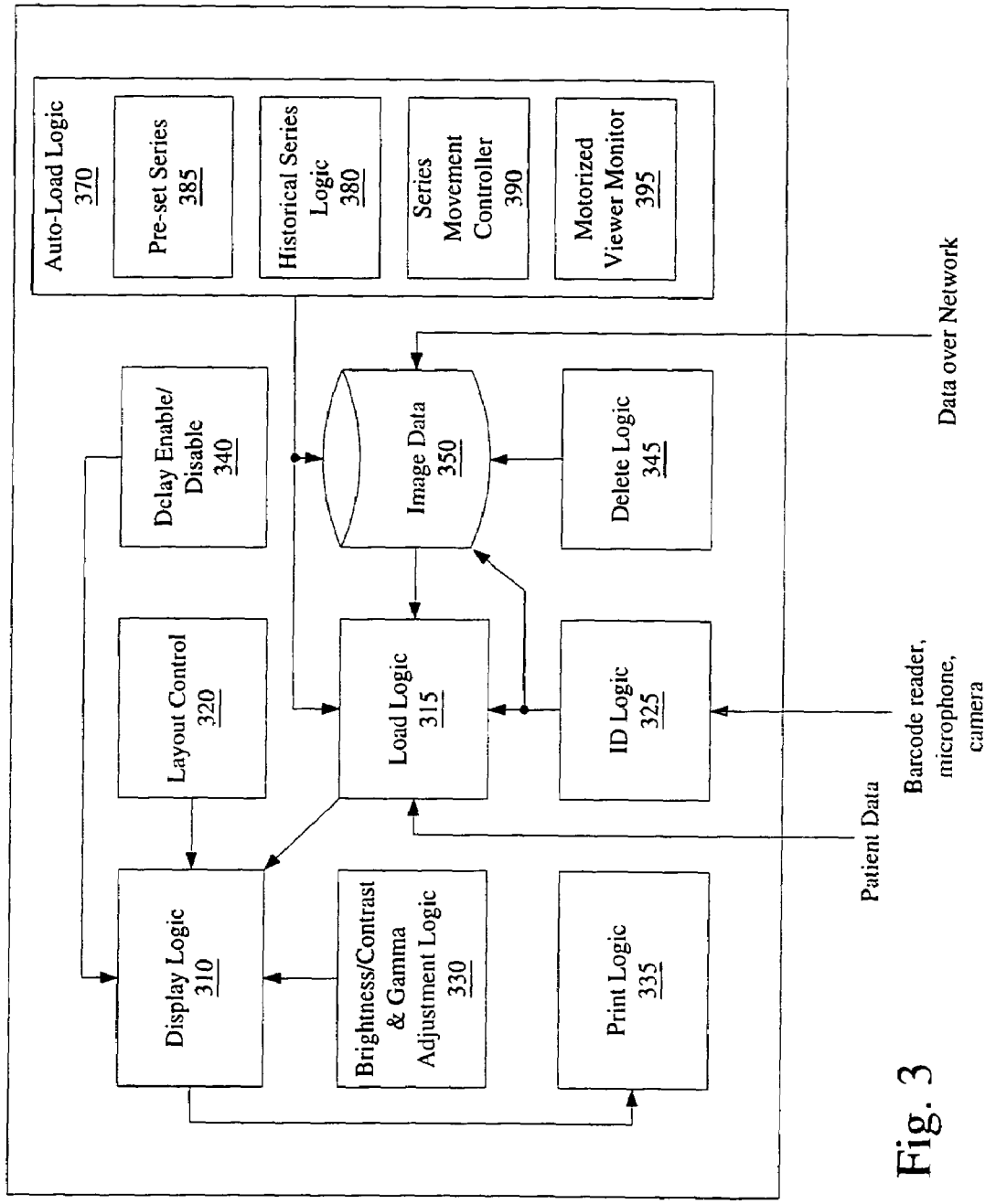
FIG. 3 is a block diagram of one embodiment of the independent display system in accordance with the present invention.
Figure 8:
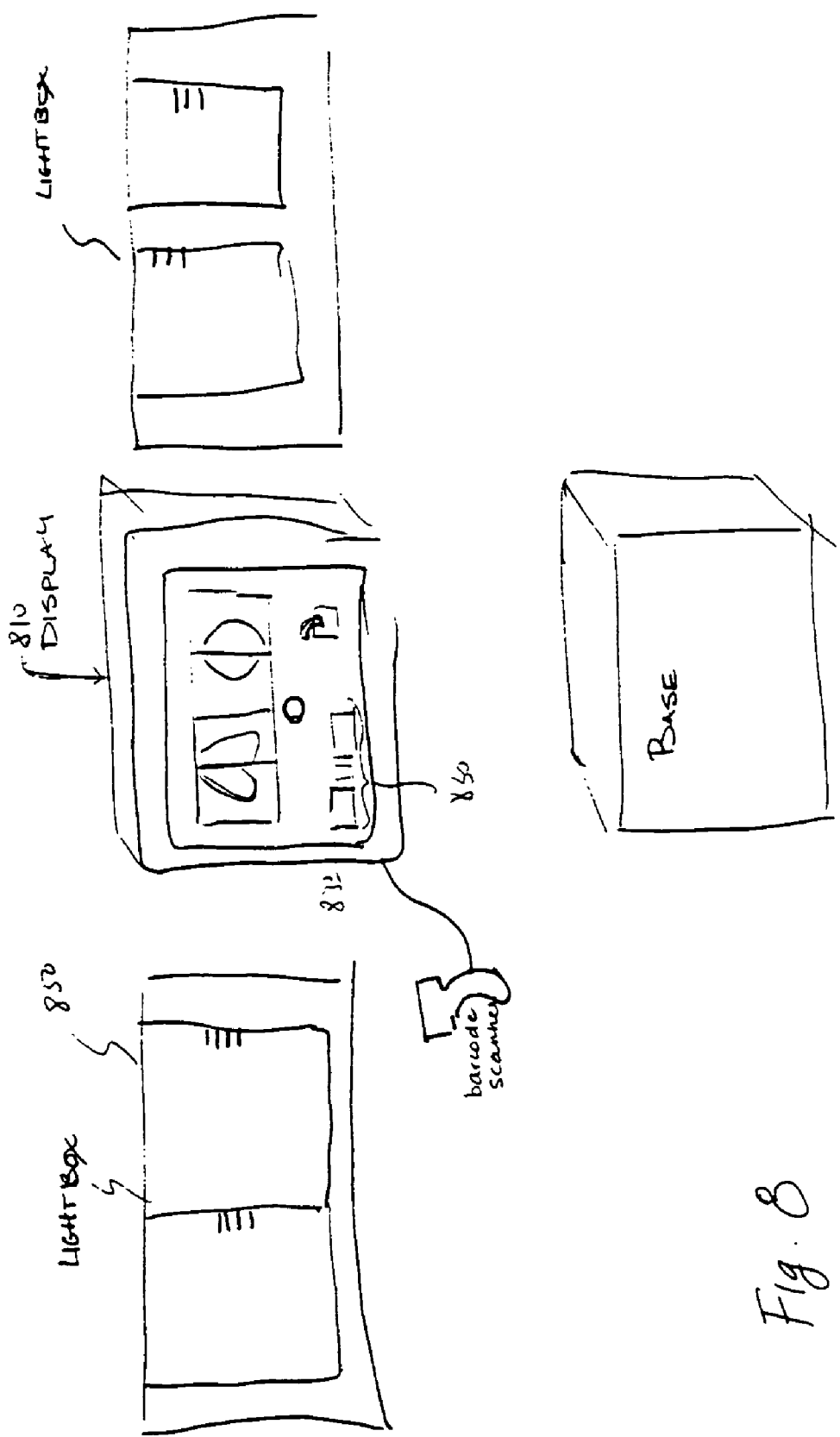

FIG. 3 is a block diagram of one embodiment of an independent review station 300. As described above, the independent review station is generally not incorporated into the standard review mechanism such as a lightbox or a motorized viewer. Rather, it is an independent display screen and associated processor that may be mounted on a table, a moveable arm, bolted to a wall, or otherwise made available to the user. For one embodiment, the independent review station 300 may include two components, a touch screen display and a system. FIG. 8 illustrates one layout. The touch screen 810 is mounted in an easily viewed location, while the base 820 of the system is placed out of the way. The below elements may be located in the base 820, or in the screen 810. FIG. 9 illustrates an alternative layout, in which the screen 910 is coupled to a wall, and connected to a frame sensor 940, which tracks the movements of a belt, panel or other moveable portion 930 of a motorized viewer. For simplicity, henceforth the term belt will refer to the moving portion of a motorized viewer to which medical images are attached.

The frame sensor 940 may monitor the movement of the belt 930 mechanically, electrically, magnetically, optically, or through some other means. Tracking the movement of an object is well known in the art, and any method that may be used, including markers on the viewer belt itself, may be used, for the frame sensor 940.

The system may further include a belt mover 950. The belt mover 950 may move the viewer belt 930, in accordance with the user's selection. In general, the motorized viewer has a belt control built in. However, for one embodiment, the user may, using independent display 910, move the belt, with mover 950. For example, as shown on FIG. 10B, the icon indicating the current frame includes arrows indicating movement to the right/left or up/down. If the user presses the arrow, for one embodiment, the belt mover 950 moves the belt in the indicated direction. This permits a reviewer to obtain the next image on the independent display while also obtaining the next frame having the appropriate medical image, with the push of a single button.

This type of causal movement makes the system useful for randomizing case viewing order, for example for clinical studies; for the location of a specific case; and permitting single button service. Note that in order to permit such an association a preprogrammed case/frame map is created when the medical images are initially hung on the viewer. Thus, the person hanging the images creates a case/frame map, which is used by the independent display system to control the images shown on the display 910, and for one embodiment to move the belt 930 as well.

The base 920, containing the processor and memory, may be stowed discretely in the vicinity of the screen 910.

The independent review station 300 includes display logic 310 to display images to a user. The display logic 310 has as inputs a control stream from the brightness/contrast and gamma adjustment (BCGA) logic 330. The BCGA logic 330 adjusts the brightness and contrast of the image being displayed. For one embodiment, the BCGA logic 330 draws the icons illustrated in FIG. 12A or 12B. For one embodiment, the user may set his or her preferences for adjusting the display by gamma or brightness/contrast. For one embodiment, the BCGA logic 330 displays touch-buttons, and monitors the user's responses on those touch buttons, as well as adjusts the image quality. For another embodiment, another transformation, either static or dynamic, may be used control the display quality.

Figure 10B:
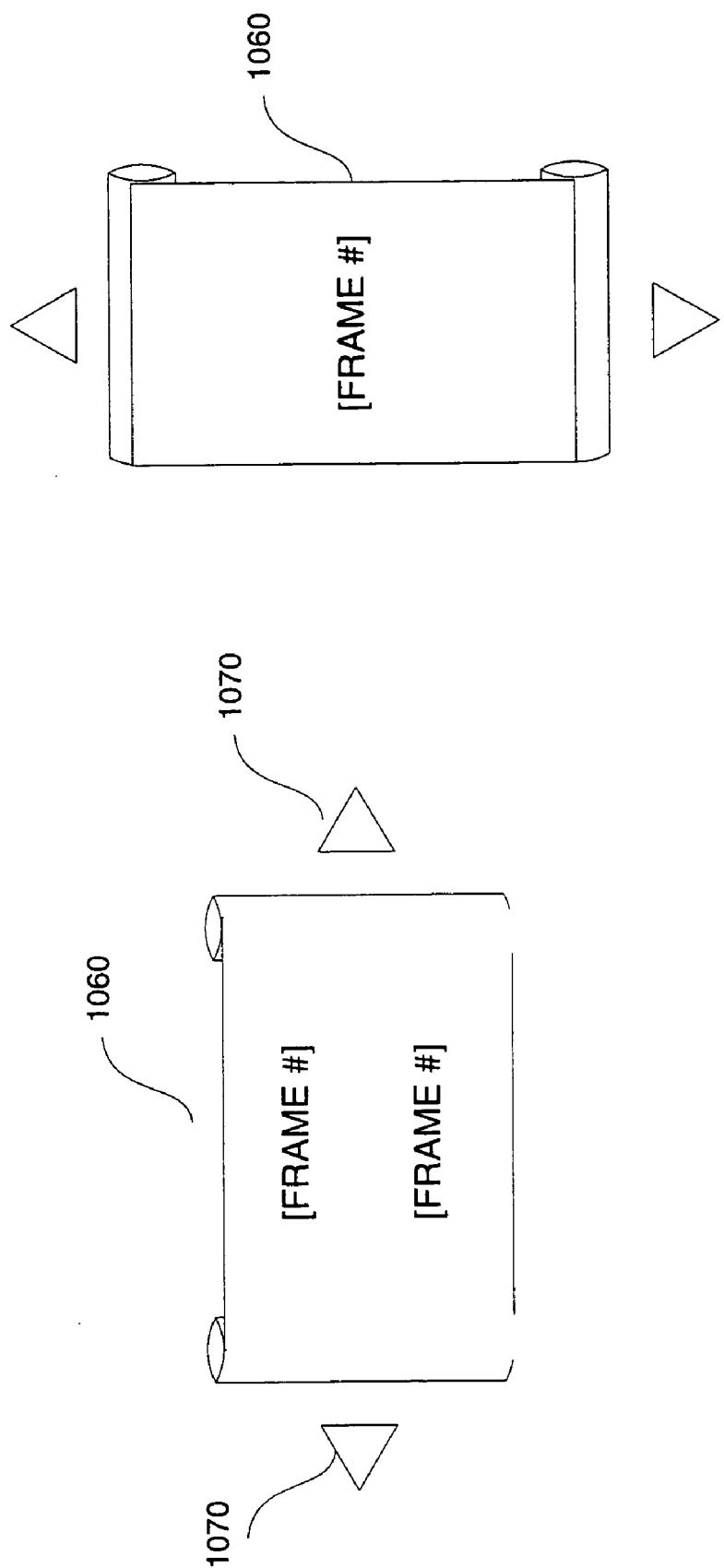
FIG. 10B is an illustration of one embodiment of various lightbox layouts and the corresponding icons.

The layout control 320 permits the user to select a location associated with the current images being displayed. As shown in the layout example on FIG. 8, the display portion of the independent review station 300 may be located between light boxes 850, 860. The actual layout of films and the light boxes, or the mechanized viewing station, varies by individual location. Thus, the layout control 320 permits the user to set the image selections to mimic the actual layout. For example, in FIG. 11A, the lightbox layout display 1130 highlights the appropriate icon 1135 corresponding to the lightbox that has the images that are being displayed on the screen. FIGS. 10A and 10B illustrate various lightbox layouts. The layout control 320 permits the user to select the lightbox to highlight, as well as to alter the basic lightbox icon.

The load logic 315 loads an image from the image data storage 350, to display logic 310. For one embodiment, the image data storage 350 may be a local disk, such as a hard drive on a computer. Alternatively, the image data storage 350 may be remote to the system, and accessible through a network connection. The load logic 315 receives image identification from ID logic 325, and determines whether it's in the local storage. If not, the load logic 315 retrieves the data from the remote site. The image data storage 350 on the local system is limited. If the newly retrieved image does not fit on the local system 350, the delete logic 345 deletes the oldest data on the local storage.

Figure 11A:
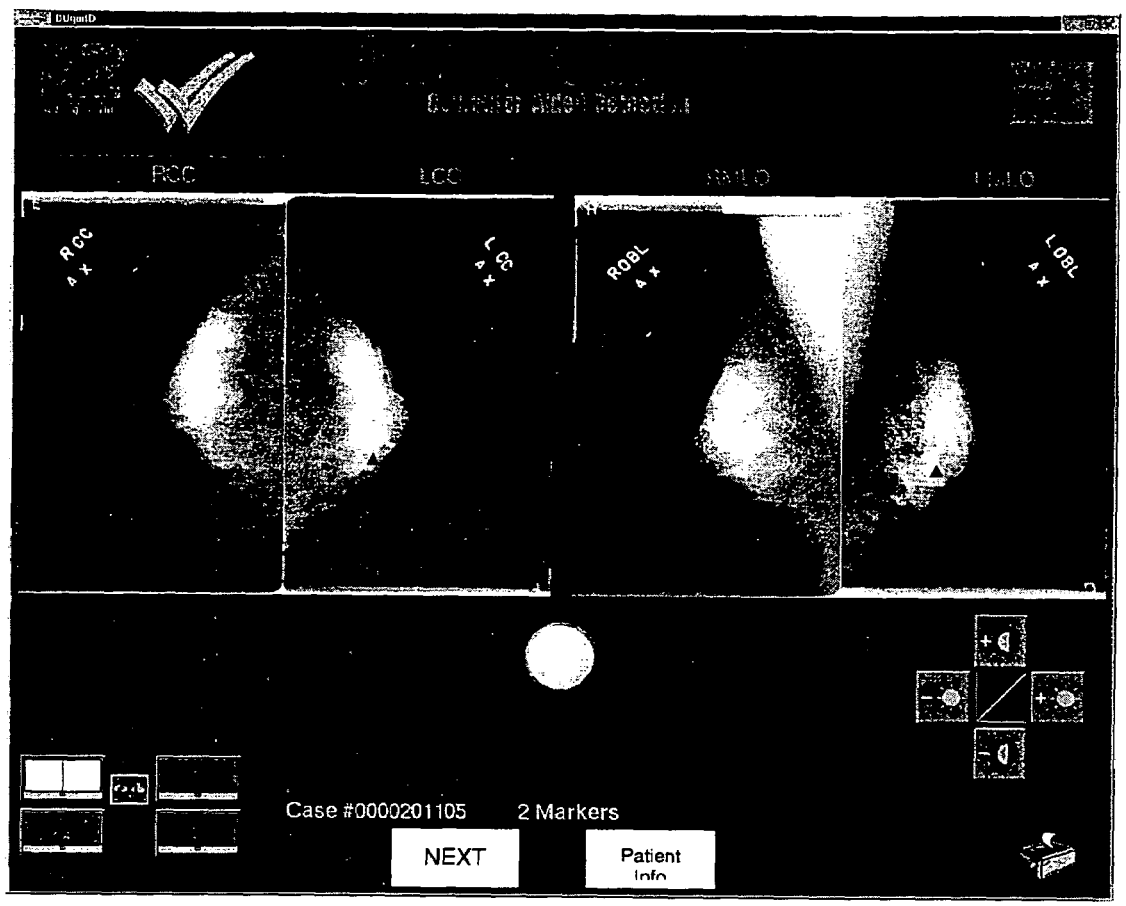
FIG. 11A is a screenshot of one embodiment of the display of an independent display system.

Load logic 315, for one embodiment, may further retrieve patient information, when the patient/image ID is received. The patient information may be patient data, including patient name, age, date of birth, etc. The patient information may further be patient history data, including the patient's history of cancer or relevant disease, family history, BRCA 1/2 or other relevant genetic markers, etc. Patient information may be loaded from the local system 350 as well, or may be retrieved remotely. The relevant patient information may be displayed, optionally, to the user. For example, for a mammogram review, the user's history of cancer, family history, BRCA marker, and other relevant information may be shown. FIG. 11A shows a toggle 1190 between the current image screen, and a patient information screen. For another embodiment, the patient history data may be displayed automatically at the same time as the image data.

The ID logic 325 provides the patient and/or image identification needed to display the correct image, corresponding to the image shown on the lightbox. The ID logic 325 receives image identification from outside the system. For one embodiment, the ID logic 325 interfaces with a barcode reader, which the user scans across a barcode associated with the image on the lightbox. The barcode may be on the image, on a sheet, on a folder associated with the patient, or in another location. Alternatively, a camera may be used to scan the barcode, patient identification on the film or other image on the lightbox. For another embodiment, voice recognition may be used by ID logic 325 to identify the patient/image.

For one embodiment, when an image ID is received, and the image data is loaded, there is a delay until the user presses a button, and/or a preset time elapses. This delay is used so that the reviewer is able to form an independent opinion, without being influenced by the displayed image, and its markers. For one embodiment, the delay may be disabled, using delay enable/disable logic 340. Because the user may initially review the images prior to scanning/entering the patient/image identification, the delay may not be needed. Thus, the user may use delay enable/disable logic 340 set the delay, or disable the delay.

The user, on reviewing the image, may use print logic 335 to print a copy of the image. For one embodiment, the print logic 335 converts the image data to PostScript or another printer readable format, prior to printing.

In general, images are displayed as the ID logic 325 receives a new image ID and the load logic 315 loads it. However, automatic pre-programmed series of images may be displayed, using auto-load logic 370.

Auto-load logic 370 permits an autoloaded series to be defined. The preset series logic 385 pre-load the image IDs for the set of images. For example, if a motorized review station is used, and the independent review station is attached to the motorized reviewer, the images that are loaded onto the motorized reviewer may be coded into the independent review station, and the preset series 385 may be defined. This removes the need for the doctor to identify subsequent images, using ID logic 325. Thus, when the doctor indicates that he or she is done with the current image, the next image is automatically loaded. For one embodiment, the series movement controller 390 displays a button on the touch screen, such that the user may indicate that he or she is done reviewing the current image by pressing a single button. For one embodiment, the Next icon is displayed, which permits the doctor to call up the next image with a single key. For one embodiment, the Next icon is only displayed when the system is running an auto-load process.

For one embodiment, when the auto-load logic 370 is used, the delay may not be disabled, to ensure that the doctor sees the physical image prior to seeing the tagged digital image including the marked ROIs.

For example, a radiologist may have a daily set of images to review. The administrator can set up the series of images to be reviewed in order. Thus, when the preset series logic 385 is running a preset series, the doctor simply indicates that he or she is done reviewing an image, using the Next selection, implemented by series movement controller 390, and the next image is automatically displayed.

For one embodiment, the series movement controller 390 may monitor the user's indication that he or she is done viewing a current image, and use the belt mover, shown in FIG. 9, to move the motorized viewer belt appropriately. Thus, the user may be able to control the movement of a motorized viewer from the independent display.

Another auto-load may be a historical series 380. This would permit a doctor to review the historical images of a particular patient. For example, if the doctor sees a suspicious region, being able to see the changes in the image over time may be helpful to determine whether the suspicious region is in fact a cancer.

Yet another auto-load feature is a motorized viewer monitor 395. The motorized viewer, show in FIG. 9 below, may be monitored using a frame sensor coupled electrically, magnetically, optically, or mechanically to the motorized viewer belt, to determine a current frame being viewed. The motorized viewer monitor 395 receives the frame number from the frame sensor, and uses the frame number to load an associated image. As discussed above, the association between frame numbers and image IDs is created prior to the reviewer accessing the images.

In this way, the user may review images on a stand-alone independent review station. The above system allows the user to adjust the lightbox icon, as well as the brightness/contrast or gamma of the image. The auto-loader permits the display of a preprogrammed series of images, with an option to view the next, previous, first, or last image in the series. The load logic loads images from a local or remote system, and may further load patient information that is relevant to the current review.

Figure 4A:
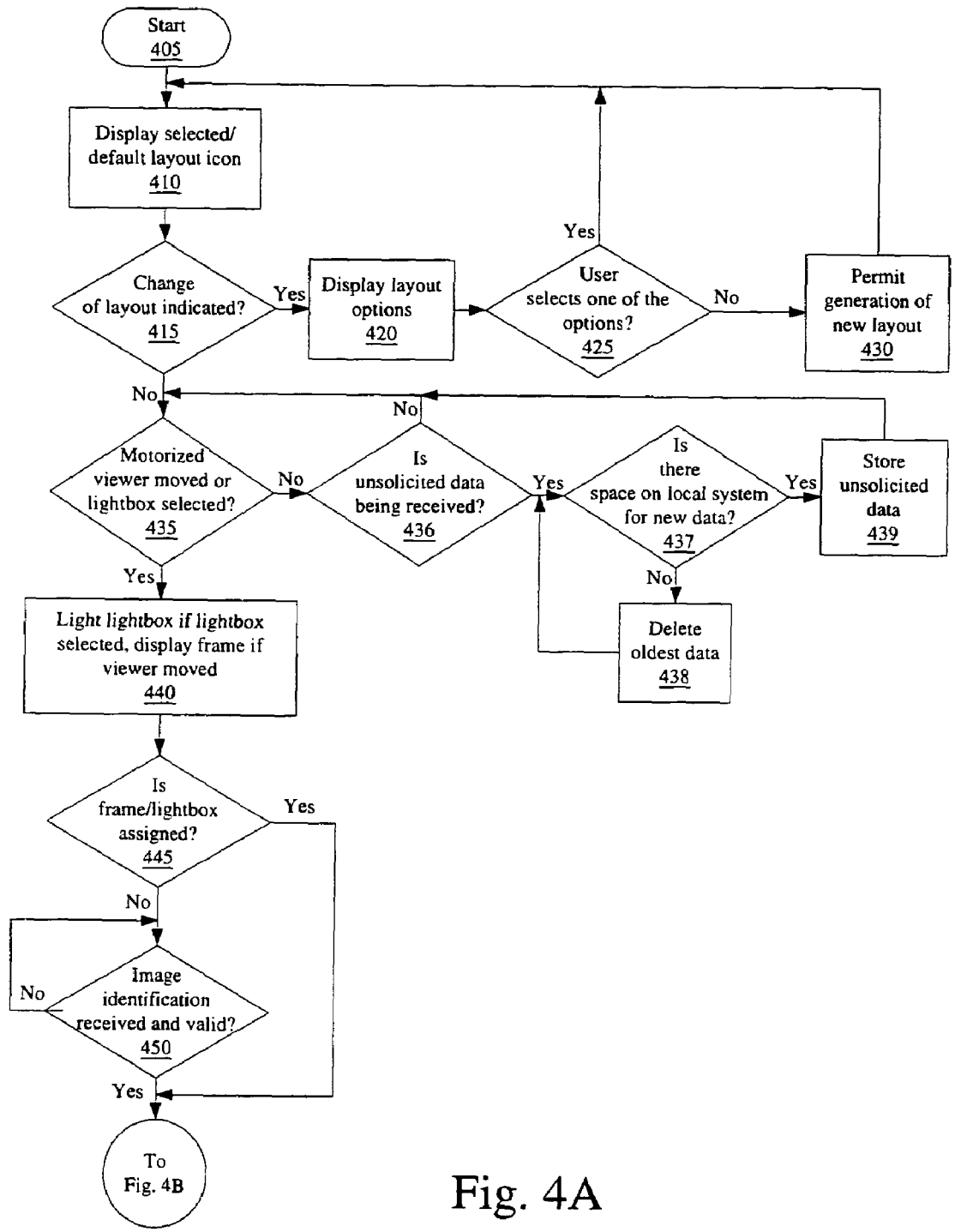
FIGS. 4 and 5 are flowcharts of one embodiment of using the independent display system.
Figure 4B:
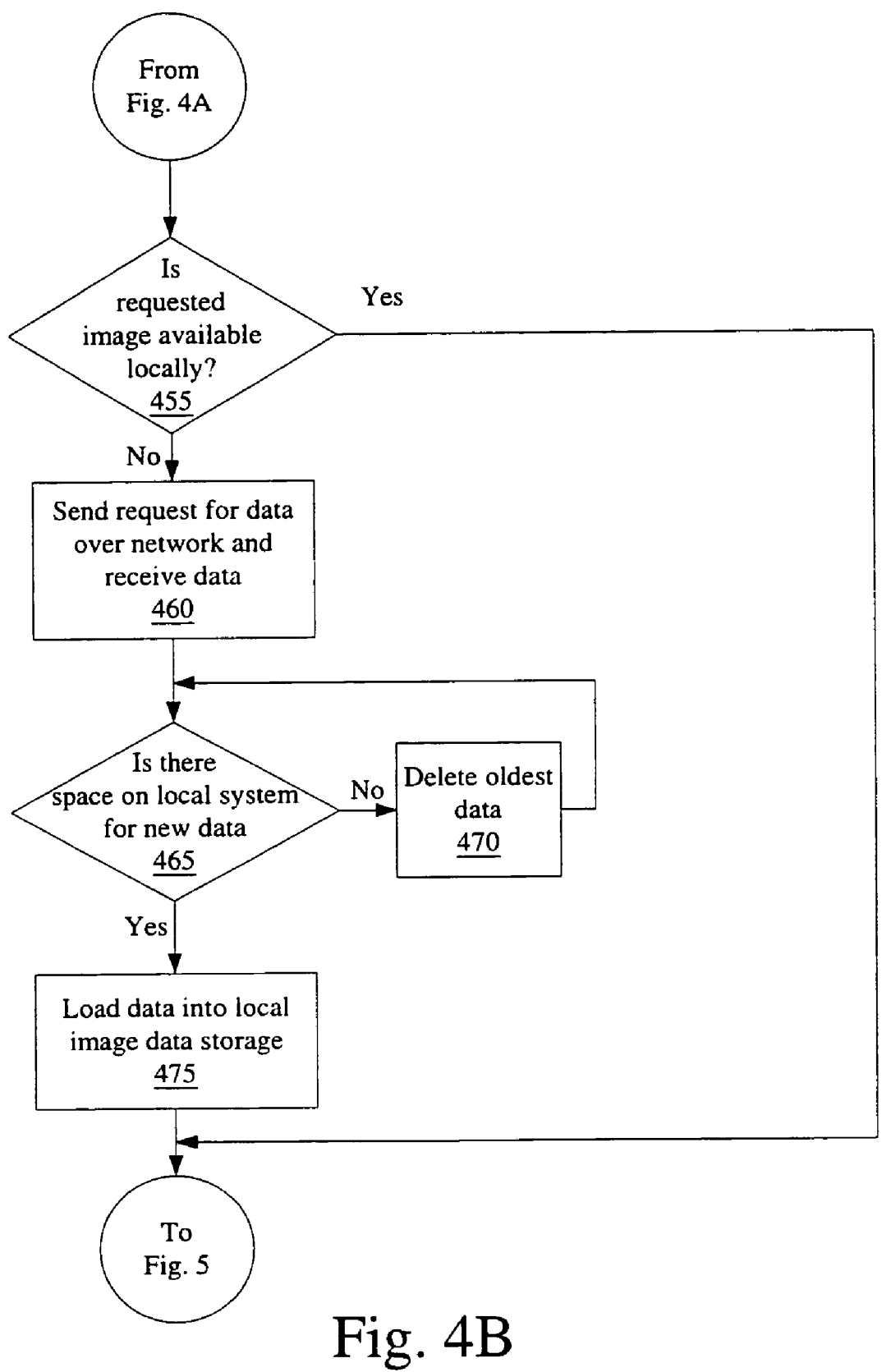
Figure 5:
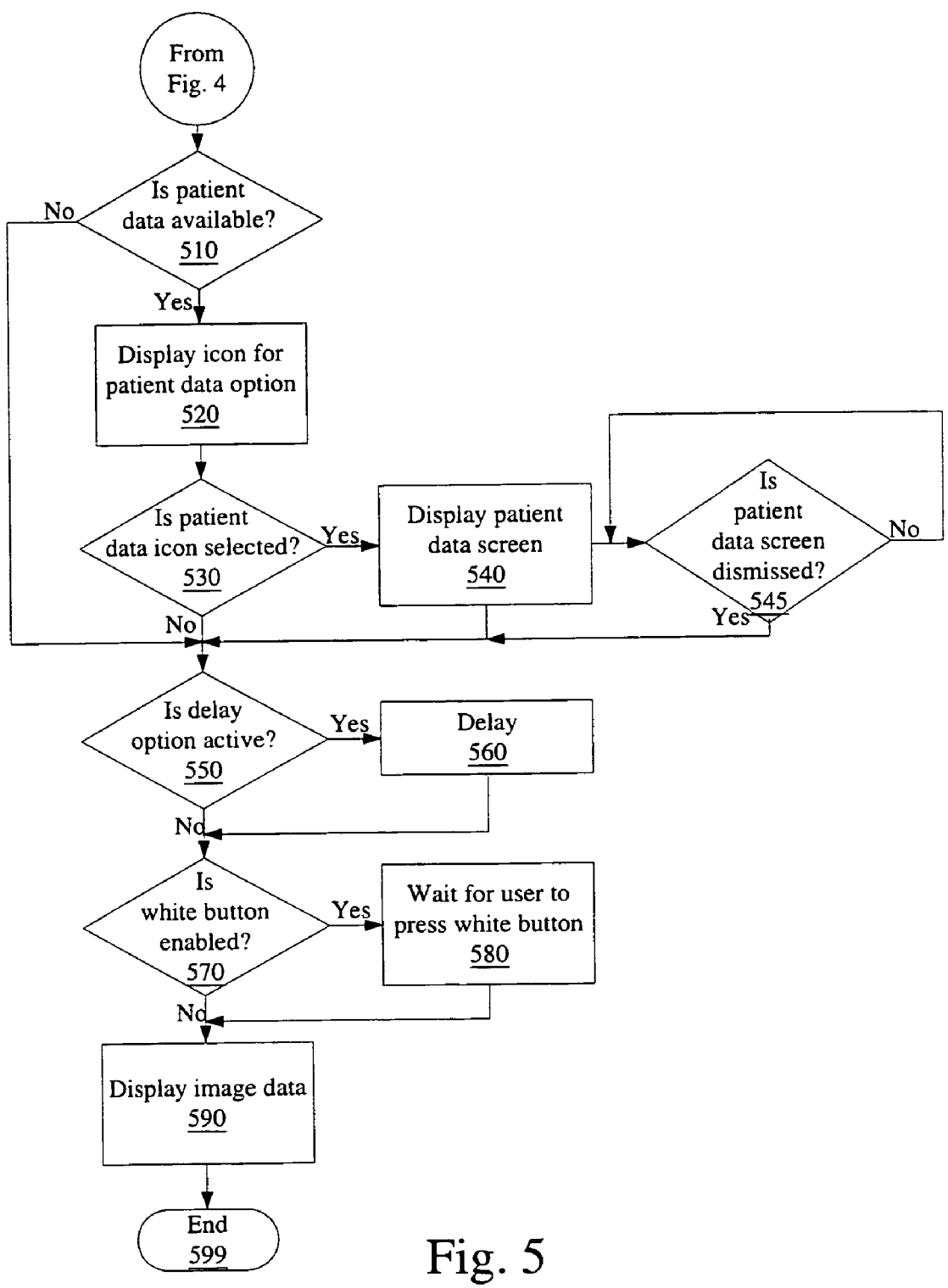

FIGS. 4 and 5 are flowcharts illustrating one embodiment of using the independent review station. The process starts at block 405, when the independent display station is initialized. At block 410, blank display is shown. The blank display does not have images on it, and displays the currently set lightbox icon.

At block 415, the process determines whether the user has indicated that he or she wishes to change the lightbox layout. In general, the user would change the lightbox layout rarely, only when the independent review station is moved, or the local layout is changed. If the user wishes to change the lightbox icon layout, the process continues to block 420. At block 420, the layout options are shown.

FIG. 10A shows one set of exemplary lightbox layout options and the corresponding icons. As can be seen, the various layout icons show the layouts available. For one embodiment, a page similar to FIG. 10A and/or 10B is shown to the user to select a layout.

FIG. 10B illustrates an alternative lightbox layout options. The lightbox layout illustrates a motorized viewer rather than a traditional light box. The icon 1060 includes the frame number, currently being displayed. As discussed above, the frame sensor may be used to indicate the frame number. Alternately, as the user moves the motorized viewer, he or she may use direction indicators 1070 to indicate next frame or previous frame. The lightbox layout may further show the layout of the motorized viewer, e.g. vertical or horizontal. For another embodiment, the lightbox layouts may correspond to those shown in FIG. 10A, with the illustration showing the motorized layouts.

Returning to FIG. 4, at block 425, the process determines whether the user has selected one of the preset layout options. If the user selects one of the layout options, the process returns to block 410, to display the selected layout icon. If the user does not select one of the layout options, at block 430, the user may design his or her own layout. For one embodiment, in order to generate a new layout, a password must be used. For one embodiment, in order to access the layout changing option—at block 415—a password must be used.

The process then returns to block 410, to display the selected lightbox icon. If the change of layout wasn't indicated at block 415, the process continues to block 435.

At block 435, the process determines whether the belt has moved on a motorized viewer or a lightbox has been selected. If the motorized viewer has not moved, or a new lightbox is not selected, the process continues to block 436. At block 436, the process determines whether the system is receiving unsolicited data. The system may periodically upload data to a local system for viewing. For example, the system may receive a set of images for review. If no unsolicited data is being received, the process returns to block 435, to wait for a movement of a motorized viewer, a lightbox selection, or unsolicited data.

If unsolicited data is being received at block 436, the process continues to block 437. At block 437, the process determines whether there is enough space on the local system for the new data being received.

If there is not enough space on the local system, at block 438, the oldest data on the system is deleted. The process then returns to block 437, to test whether there is now adequate space to store the new data. If there is enough space, the process continues to block 438. At block 438, the new data is stored on the local system. The process then returns to block 435.

If, at block 435, a lightbox has been selected, the process, at block 440 highlights the selected lightbox. If the belt has moved, the frame associated with the currently viewed location of the belt is displayed, at block 440. This is shown in FIG. 9 below. The process then continues to block 445.

At block 445, the process determines whether the lightbox is assigned. If so, the process continues directly to block 455. Otherwise, the process continues to block 450.

At block 450, the process determines whether a valid image identification has been received. A valid image identification identifies the image(s) that should be displayed. The process waits until a valid image identification has been received. The process then continues to block 455. For one embodiment, the process times out after a preset period, and the system goes to sleep. Otherwise, the process continues to block 455.

At block 455, the process determines whether the image data is available locally, e.g. stored in image data 350. If the image data is available locally, the process continues. The continuation of this process is shown in block 510 in FIG. 5. If the image is not in local memory, the process continues to block 460.

At block 460, a request for the data is sent over the network, and the response is received. For one embodiment, the request is sent to a main database. For another embodiment, the data may be stored in a distributed system, as is known in the art.

At block 465, the process determines whether there is adequate space on the local system for the new data. If there is not enough data to store the newly received data, the process continues to block 470.

At block 470, the oldest data on the system is deleted. The process then returns to block 465, to test whether there is now adequate space to store the new data. If there is enough space, the process continues to block 475. At block 475, the new data is stored on the local system. The process then continues to block 510, of FIG. 5.

At block 510, the process determines whether patient information is available. Patient data may be available if data is stored in DICOM format. Furthermore, the user may set a preference as to the availability of patient information. If patient information is not available, the process continues to block 550. Otherwise, the process continues to block 520.

At block 520, the icon for patient information option is displayed on the screen. For one embodiment, an "Additional Patient Data" button may be displayed. Alternatively, the button may be continuously displayed, but only lit or active when patient information is available. In that case, at this point, the patient information option button is highlighted and made active.

At block 530, the process determines whether the patient information icon is selected. If so, at block 540, the patient information is displayed to the user. For one embodiment, the patient information is displayed on a separate screen. For another embodiment, the patient information may be displayed in a separate window on the same screen. For yet another embodiment, the patient information may be displayed on the same screen as the image data. If the icon is not selected, or after the patient data is displayed and the user dismisses the patient data screen at block 545, the process continues to block 550. For another embodiment, the patient information may be automatically displayed, if it is available. In that instance, blocks 530 and 545 are removed, and the process continues directly from block 520 to block 540.

At block 550, the process determines whether the delay option is active. If so, at block 560, the system waits for the delay to expire. The process then continues to block 570. If the delay option is not active, the process continues directly to block 570.

At block 570, the process determines whether the white button is enabled. The white button requires a positive action from the user, e.g. pressing the white button, to display an image. Note that although the button is referred to as a "white button" it may be any color, and may be any action, e.g. a button, a keystroke, a hotkey, etc. Using the white button ensures that the user has had a chance to review the image without being influenced by the markings shown in the processed image. However, in the independent display, this option may be disabled—since the user identifies the images, which may provide sufficient time to do an independent analysis. If the white button is enabled, the process continues to block 580.

At block 580, the process waits for the user to press the white button. The process then continues to block 590. If the white button is disabled, the process continues directly to block 590. At block 590, the image data is displayed. The display process then ends at block 580.

Note that although the above options are described sequentially, and as decision blocks, much of the above processing takes place simultaneously. Thus, for example, the system does not loop in an infinite cycle until patient information is received. Rather, the patient information receipt may be an interrupt that activates the process. Additionally, the queries for image data and patient information may be performed in parallel. Furthermore, the patient information icon may be selected at any time during the viewing process.

Figure 6A:
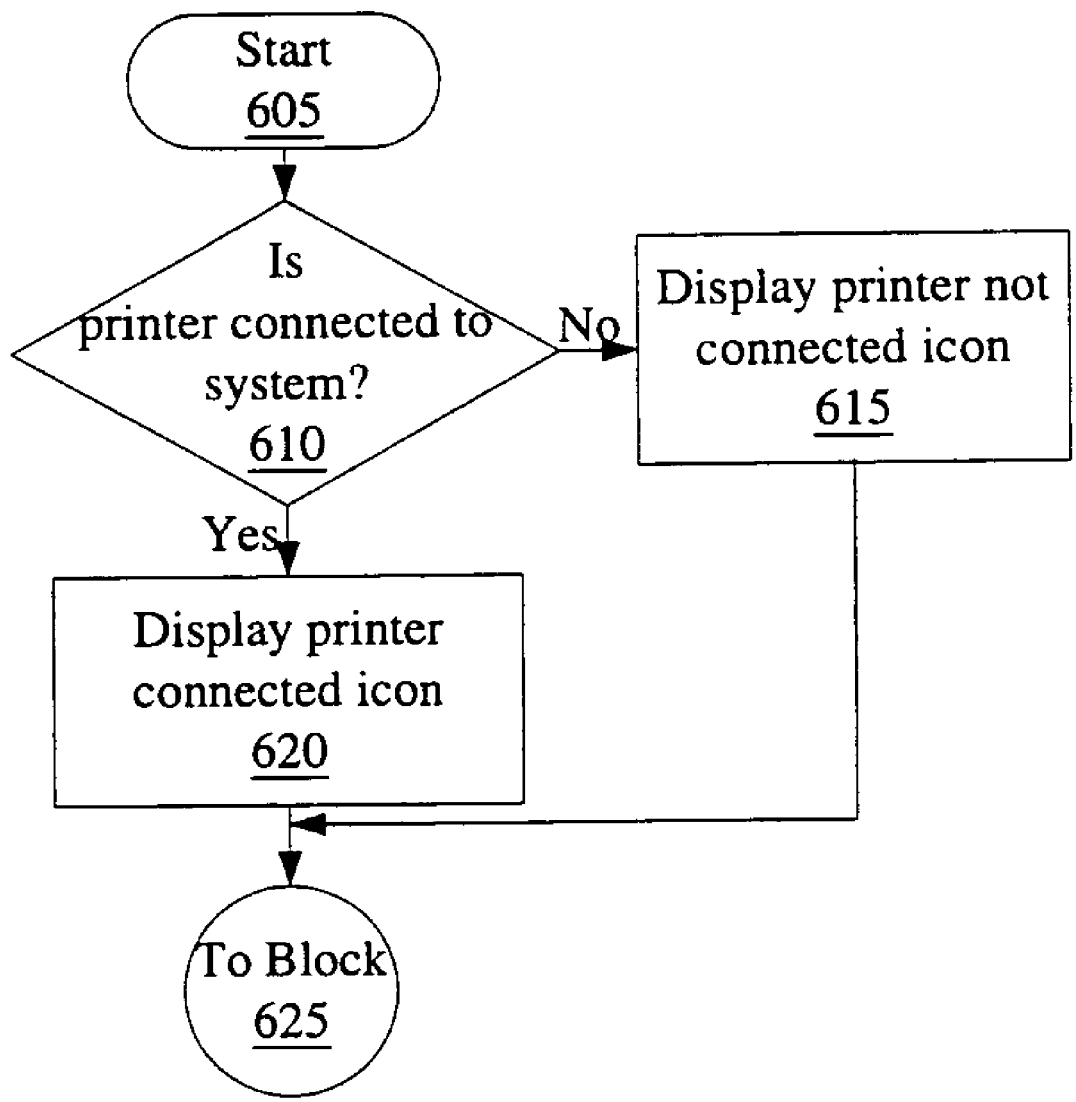
FIGS. 6A and B are a flowchart of one embodiment of adjusting the display of the independent display system.
Figure 6B:
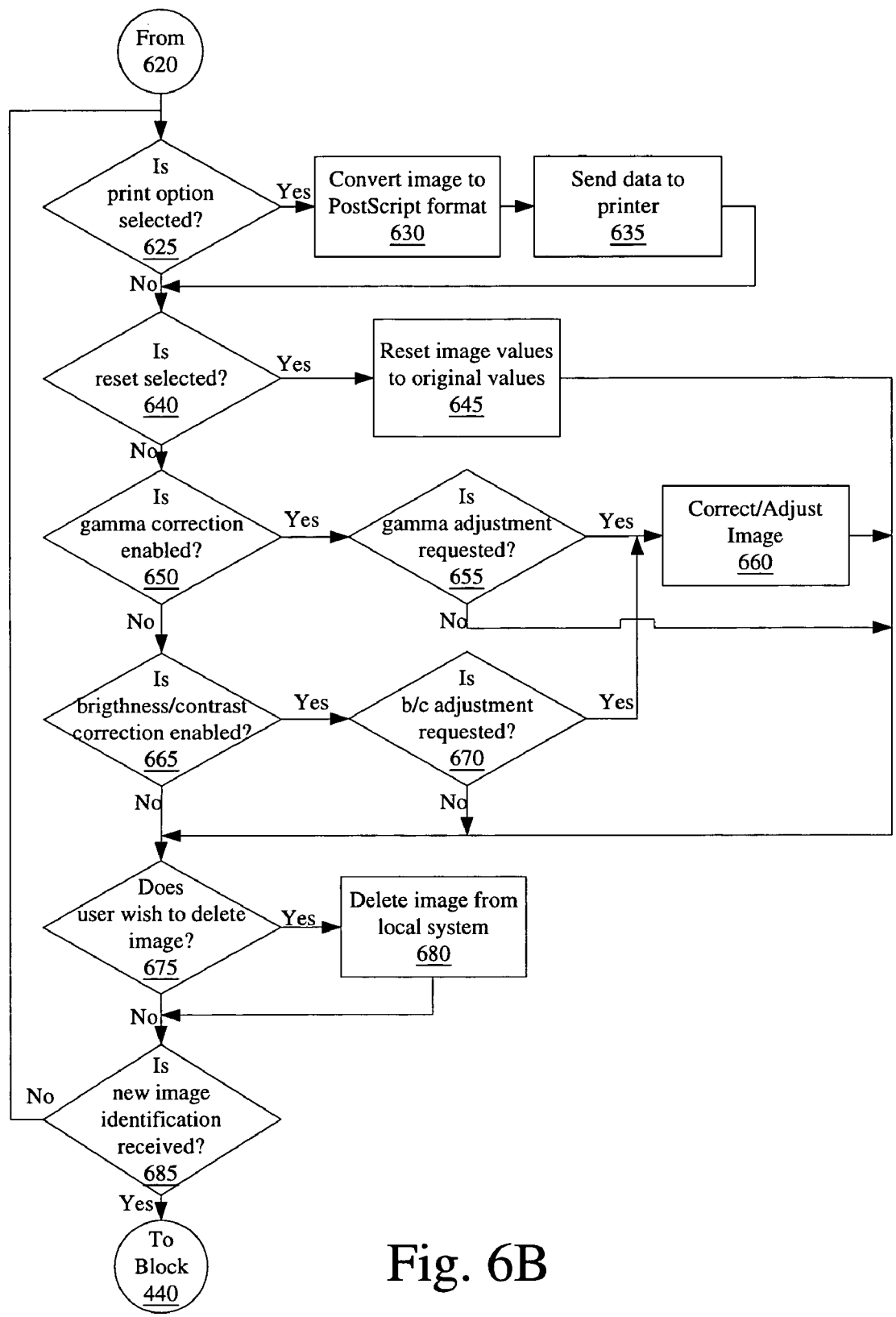

FIGS. 6A and B are a flowchart of one embodiment of adjusting the display. The process starts at block 605, when the processes described above with respect to FIGS. 4 and 5 have been completed, and the image is being displayed for review/verification. FIG. 11A shows a screenshot of an image being displayed in accordance with one embodiment of the present invention.

At block 610, the process tests whether the printer is connected to the system. Such a system test is well known in the art. If the printer is not connected, the process continues to block 615. At block 615, the printer icon displayed is the "printer not available" icon. Otherwise, at block 620, the printer available icon is displayed. The printer icon, shown as item 1160 in FIG. 11A, has two versions. The version shown in FIG. 11A indicates that the printer is connected and available to print. For one embodiment, the alternative version shows a line through the printer, and does not show the paper coming out of the printer. Alternate methods of indicating that the printer is available or not available may be used. The process then continues to block 625.

At block 625, the process determines whether the user has selected the printer option. The printer option may be selected by touching the printer icon—if the printer is connected. If the printer option is selected, the process continues to block 630. At block 630, the image is converted to a printer readable format. For one embodiment, the format is a PostScript format. Alternative formats may be used. At block 635, the data is sent to the printer. The process then returns to block 640. If the user did not select the printer option, the process continues directly to block 640.

At block 640, the process determines whether a reset is selected. The user may select to return to the original image quality, e.g. by resetting the brightness/contrast or gamma settings. If the user chooses to do so, the process continues to block 645, where with a single button, the original parameters are reset. As shown in FIGS. 12A and 12B, the center of the control buttons, showing the diagonal line, is the reset button. This permits a rapid reset, without having to find the actual original settings. The process then continues to block 675.

If the user does not wish to reset the images, the process continues to block 650. At block 650, the process determines whether gamma correction is enabled. The user may set gamma correction, brightness/contrast adjustment, or alternative methods of adjusting the image quality. For one embodiment, the icons 1240, 1245 shown in FIG. 12B are displayed, if gamma correction is enabled. If gamma correction is enabled, the process continues to block 655.

At block 655, the process tests whether gamma correction is selected. If the user tries to use gamma correction, by pressing one of the icons 1240, 1245 gamma plus or gamma minus, the process continues to block 660. At block 660, the image quality is adjusted. If the user does not select gamma correction, the process continues directly to block 675.

As shown in FIG. 12B, the curve illustrating the current settings 1250, in the center of the icon, is appropriately adjusted. If the gamma is increased, the curve 1260 becomes convex, while if gamma is decreased, the curve 1265 becomes concave. The process then continues to block 675.

If the gamma correction is not enabled at block 650, the process continues to block 665. At block 665, the process determines whether the brightness and/or contrast correction is enabled. If so, the process continues to block 670. At block 670, the process determines whether the user is requesting to adjust the brightness and/or contrast. If the user does not select brightness/contrast correction, the process continues directly to block 675.

In that instance, the icons 1210, 1215, 1220, 1225 shown in FIG. 12A are displayed. Note that in general, one or the other set of icons is pre-selected for display. Thus, the user generally only has either gamma or brightness/contrast adjustment available. Alternative formats of adjustment may be available and implemented in a similar manner.

If the user wishes to adjust the brightness/contrast, by pressing one or more of the icons, the process continues to block 660. At block 660, the image quality is adjusted in accordance with the user's adjustments. The process then continues to block 675.

As shown in FIG. 12A, the curve illustrating the current settings 1230, in the center of the icon, is appropriately adjusted. If the brightness is increased, the curve 1270 is shifted forward, while if contrast is increased the curve 1270 becomes steeper. Conversely, if brightness is decreased, the curve 1280 is sifted back, and if contrast is decreased, the curve becomes less steep.

For one embodiment, the brightness/contrast and/or gamma adjustments may be made numerically rather than by pressing buttons. Thus, the display may be showing a gamma value (equation of the slope), or an assigned value for brightness and contrast, such as 50 for each. The user can then enter in a preferred setting, i.e. adjust the equation or alter the brightness and/or the contrast.

At block 675, the process determines whether the user wishes to delete the image. If so, at block 680, the image is deleted from the local system. For one embodiment, this deletion may be propagated to the main system as well. If the user does not wish to delete the image, the process continues to block 685.

At block 685, the process tests whether new image identification has been received, indicating that a new image is to be displayed. If new image identification has been received, the process goes to block 440, in FIG. 4, as described above. If no new image identification is received, the process returns to block 625.

Note that although the above options are described sequentially, and as decision blocks, much of the above processing takes place simultaneously. Thus, for example, the system does not sequentially query whether the print options are available, gamma/brightness/contrast controls are selected, or deletion is selected. Rather, the system is, for one embodiment, interrupt driven. Thus, if a particular signal is received, such as gamma adjustment or printing, the associated steps are taken. The above-described process permits easy adjustment of the image, and manipulation of the input and output.

Figure 7A:
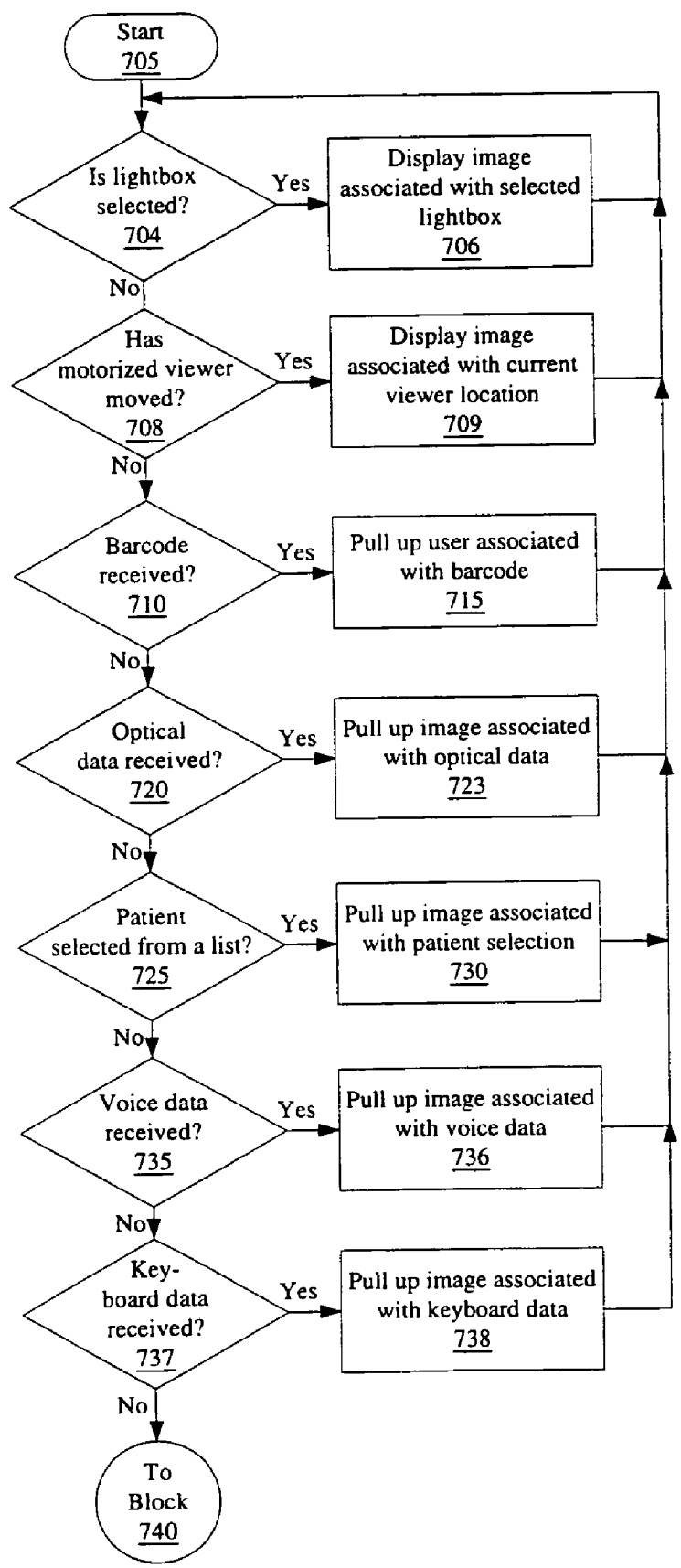
FIGS. 7A and B are a flowchart of one embodiment of receiving image data for the independent display system.

FIGS. 7A and B illustrate one embodiment of loading an image. This corresponds to block 435, in FIG. 4. The process starts at block 700.

At block 704, the process determines whether a lightbox is selected. If so, the process continues to block 706, and the image last associated with the selected lightbox is displayed. The process then returns to block 704, to start the series again.

If, at block 704, the lightbox is not selected, the process continues to block 708. At block 708, the process determines whether the motorized viewer belt has moved. If so, the image associated with the current belt location, e.g. frame, is displayed at block 709. The process then returns to block 704. Otherwise, the process continues to block 710.

At block 710, the process determines whether a barcode is received. For one embodiment, a bar code scanner is attached to the independent review station, and the user may scan the barcode. For one embodiment, a barcode is physically attached to an image. For another embodiment, the folder in which the images come include a barcode. For another embodiment, a card including the barcode is included with the images and barcodes are reused after the image expires. Thus, as the user moves the figures from the folder to the lightbox for viewing, he or she may scan the barcode, using the barcode scanner. For one embodiment, the scanner may be attached such that as the images are placed on the lightbox, the associated barcode is automatically scanned.

If a barcode is received at block 710, the process continues to block 715. At block 715, the image associated with the barcode is retrieved. For one embodiment, the image may be multiple images. For example, a mammogram image is a set of four images, showing the left and right breast from two positions. The term "image" is to be understood as a set of one or more images that are associated with a particular patient and a particular testing series. Thus, for example, an image for a mammogram may include eight images, if two sets of tests were run on an individual in the same session, while a CT scan may include dozens of images.

Note that the process of retrieving the images is described in more detail with respect to FIG. 4. The process then returns to block 704, to restart the series.

If no barcode is received, at block 710, the process, at block 720, the process determines whether a patient is selected from a list. For one embodiment, a list of potential patients may be displayed to the user. This may be done in response to a preprogrammed set of patients, or listing all patients about whom patient information is available. The user then can select a patient, by touching the name/listing, selecting with a stylus or keyboard, or by another means. If the patient was selected from a list, the process continues to block 723. At block 723, the image associated with the patient whose name was selected is loaded. The process then returns to block 704.

If patient information is not selected from a list at block 720, the process continues to block 725. At block 725, the process determines whether image data has been received from an image acquisition device. The image acquisition device may be a camera, or similar device. The data may be received from a camera or other mechanism that reads the patient data from the individual films/images on the lightbox. If the data has been received, the process continues to block 730. At block 730, the images associated with the data are retrieved, and the process returns to block 704, to restart the series.

If image data is not received, at block 725, the process continues to block 735. At block 735, the process determines whether voice data has been received, identifying the image. The system may include a voice recognition element that permits the user to read off the image number, or the patient data, to obtain the corresponding images. If voice data is received, and properly analyzed, the process continues to block 736, where the images associated with the data are retrieved. The process then returns to block 704, to restart the series.

If no voice data is received at block 735, the process continues to block 737. At block 737, the process determines whether keyboard data has been received. The user may enter the image ID using a keyboard, either physically coupled to the system, or displayed on the touch screen. If keyboard data is received, the process continues to block 738, where the images associated with the data are retrieved. The process then returns to block 704 to restart the series.

If no keyboard data is received at block 737, the process continues to block 740.

At block 740, the process determines whether a historical data has been requested for the current patient. The user, on seeing a current set of images, may request the historical data for the patient. By reviewing the historical, data the user may be better able to determine whether a region of interest (ROI) is actually relevant. If the user requested historical data, the process continues to block 745.

Figure 11B:
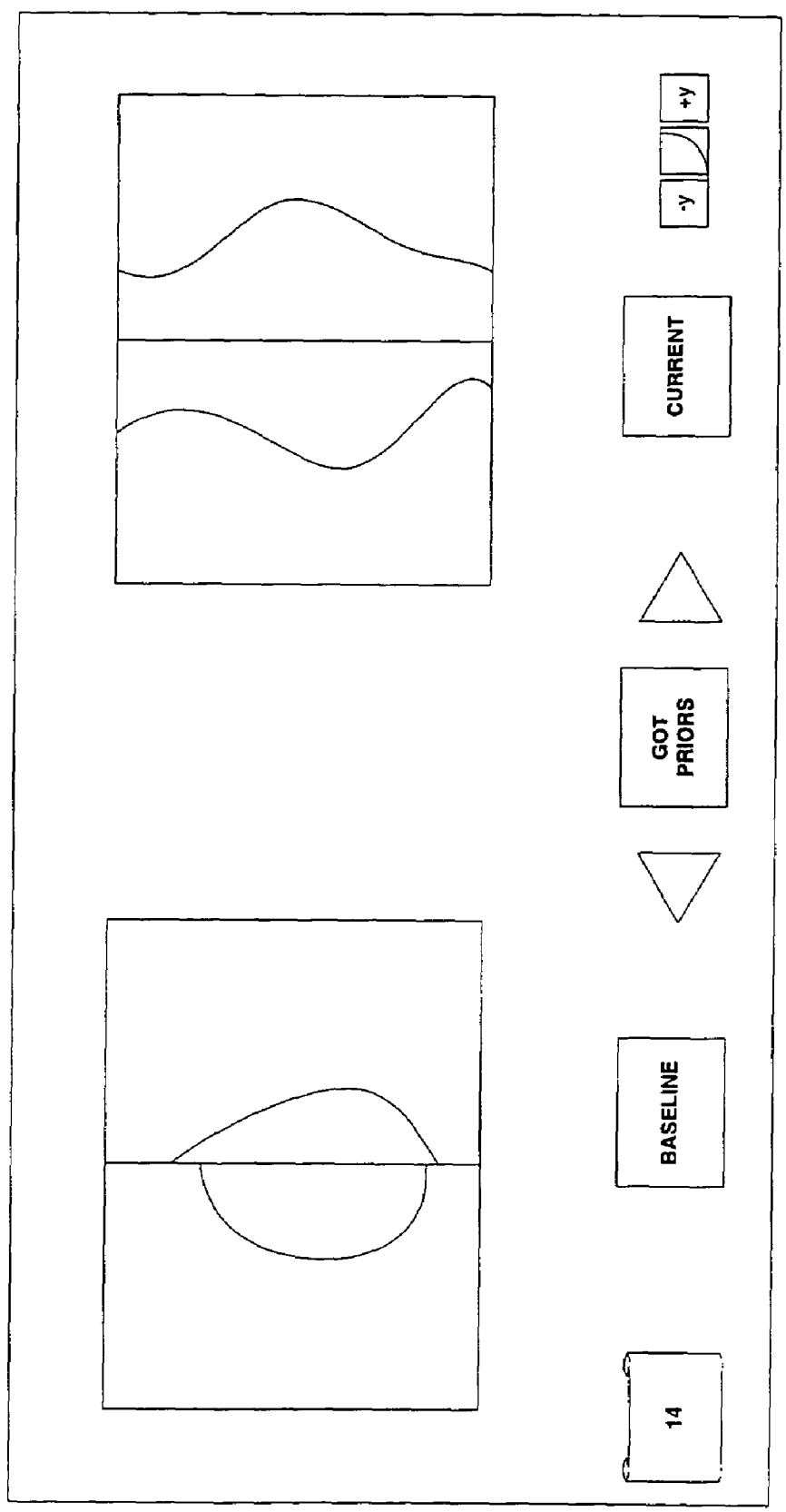
FIG. 11B is an illustration of another embodiment of the display of an independent display system.

FIG. 11B illustrates one embodiment of the user interface including the historical data access. The "get priors" button 1170 indicates that prior data is available. When the user selects the "get priors" button 1170, the historical images are loaded, as discussed below. For one embodiment, the "get priors" button 1170 is disabled once historical images are loaded. The user can then navigate from the baseline image 1190 to the current image 1195, using forward 1180 and back 1180 buttons, as well as the current 1195 and baseline 1190 buttons. For one embodiment, when the user is at the current image, the forward button 1180 is disabled, and vice versa.

Figure 7B:
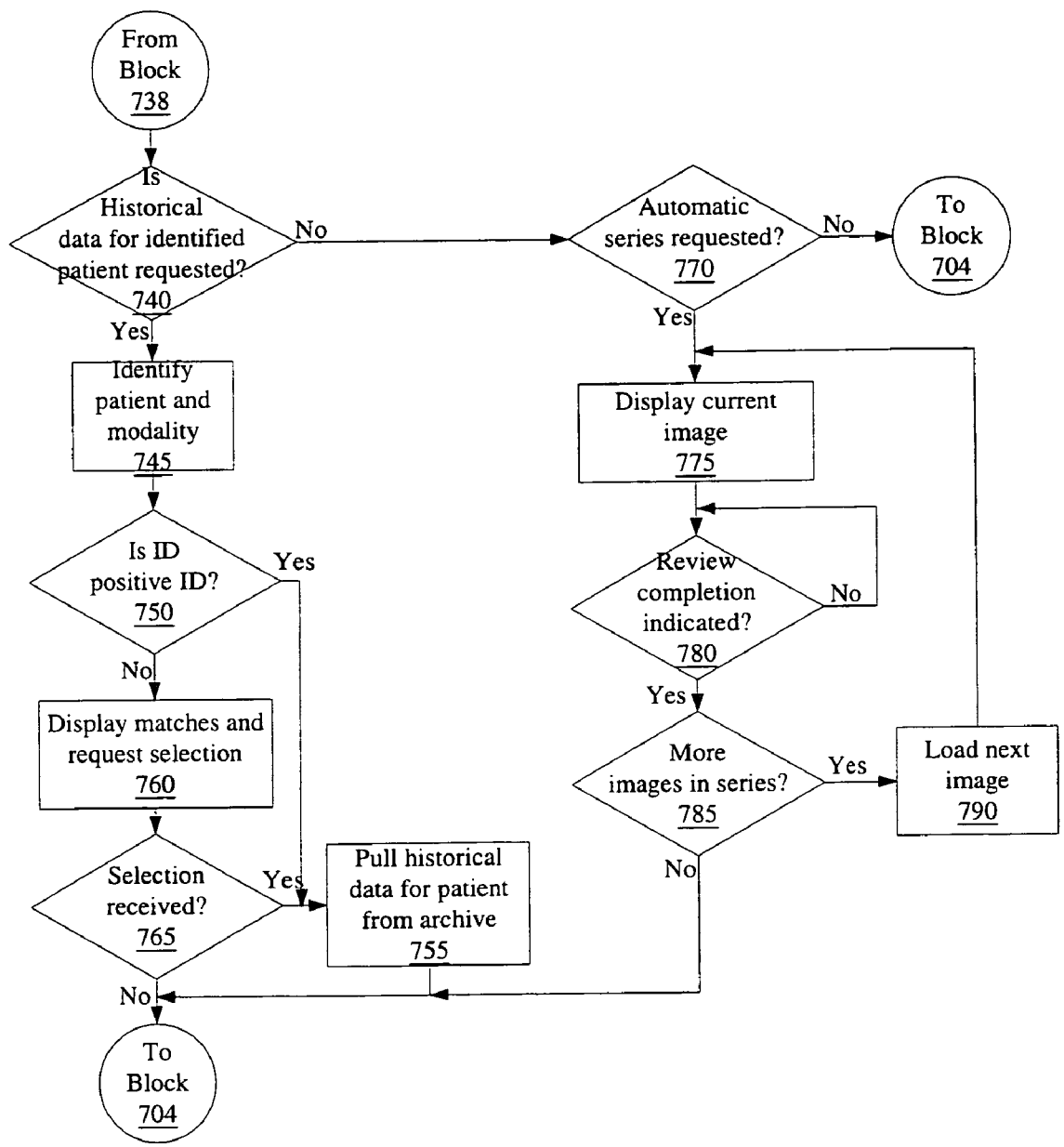

Returning to FIG. 7, at block 745, the patient and modality is identified. As discussed above, the bar code or other identification of the particular image is matched to a patient. Furthermore, since the system is modality independent, multiple types of historical images may be available, i.e. mammograms, CT scans, etc.

For one embodiment, the patient and the modality can be identified based on the image identification associated with the current image. Note that for one embodiment, the patient identity is not associated with the bar code or image identifier. In that instance, this particular process may not be available. Similarly, if historical images are not stored, this feature may not be available. If the process is available, the patient and the modality are identified, at block 745.

At block 750, the process determines whether the identification is a positive identification. Potentially, multiple patients and multiple potential modalities may be matched by the current image. For example, if the data is imprecise, e.g. 4 of 5 ID numbers matched, the identification may have more than one potential match.

If the identification is not a positive identification, the process continues to block 760. At block 760, the process displays the potential matches and requests a selection from the user. If, at block 765, a selection is received, the process continues to block 755, where historical data for the patient is pulled from the archive. If no selection is received over a time, the system may time out, and the process may return to block 704 to restart the cycle.

If the identification was a positive identification of the patient and modality, at block 750, the process continued directly to block 755. At block 755, the historical images for the patient and modality are retrieved from the archive. The process then returns to block 704, to restart the series.

If, at block 740, historical data was not requested, the process continued to block 770. At block 770, the process determines whether an automatic series has been set up, and is active. As discussed above, automatic series permit the doctor to view a series of images without having to call up and/or identify each image. This is especially useful in conjunction with a motorized viewer, since the images on the belt are known ahead of time, and are set up by an administrator.

If the automatic series is not requested, the process returns to block 704, to restart the series. Otherwise, the process continues to block 775.

At block 775, the current image is displayed. The current image is the next image in the series.

At block 780, the process determines whether the review completion has been indicated by the user. The user may indicate that he or she has completed the review of the image by moving the motorized viewer belt to a next image, scanning a new image ID, pressing a next/done key, or by other means. For one embodiment, the user must indicate that he or she has completed the review of the current image. If the user has not indicated review completion, the process waits for the user to indicate review completion. For one embodiment, after a period of time, the process may time out, and the automatic series may be stopped.

Once the indication that the review has been complete is received, at block 780, the process continues to block 785.

At block 785, the process determines whether there are more images in the series in the chosen direction. If the series has been completed, and all images have been displayed, the process returns to block 704, to restart the series. Otherwise, the process continues to block 790. At block 790, the next image in the series is loaded and designated as the current image. For one embodiment, in order to permit the user to review the new image without looking at the marked ROIs, a delay is built into the system. Thus, either the user may press a "display now" button to activate the display, or the image may be displayed automatically after a short delay.

The process then continues to block 775, where the current image is displayed. In this way, the automatic series permits the system to automatically load subsequent images as the user indicates that the past image has been analyzed. The process continues until, at block 785, no more images are found. At that point, the process ends.

The above process describes various ways of loading images, based on various inputs. Note that although the above inputs are described in flowchart form as a series of queries, this type of process is generally interrupt driven. Furthermore, in general, a single system may use only one of the above types of inputs. Thus, for example, a system may be configured to accept only barcode inputs. Alternatively, all of the above described options may be available, if the appropriate input mechanism—e.g. a bar code scanner, a camera image acquisition mechanism, and/or a microphone are available. Additional input mechanisms including typed entries and other inputs may by used to identify the image.

In the foregoing specification, the invention has been described with reference to specific exemplary embodiments thereof. It will, however, be evident that various modifications and changes may be made thereto without departing from the broader spirit and scope of the invention as set forth in the appended claims. The specification and drawings are, accordingly, to be regarded in an illustrative rather than a restrictive sense.

What is claimed is:

1. An independent display system for a computer aided detection (CAD) system that analyzes medical images, the independent display system comprising:
    an autoload logic to enable a technician to individually associate a plurality of CAD-processed digitized medical images with a corresponding plurality of lightbox buttons, the lightbox buttons being spatially arranged within a lightbox icon to reflect a physical arrangement of a plurality of lightboxes on which a plurality of film-based medical images from which said digitized medical images have been derived are placed;
    an input mechanism to receive an image identifier for each of said film-based medical images during said individual associations;
    a touch screen to display the digitized medical images including any marked regions of interest;
    a plurality of icons to interact with the touch screen, such that the independent display system does not require a keyboard or cursor controller;
    one of the plurality of icons including said lightbox icon, wherein one of the lightbox buttons is selected by a radiologist to bring up the digitized medical image corresponding to a currently examined one of the film-based medical images.

2. The independent display system of claim 1, wherein the digitized medical images remains associated with the lightbox buttons on the lightbox icon, such that previous images are recalled by selecting the appropriate lightbox button.

3. The independent display system of claim 1, wherein lightbox icon:
    illustrates the independent display system positioned in proximity to said light boxes as represented by said lightbox buttons, reflecting an actual layout in a current location.

4. The independent display system of claim 1, further comprising:
    a layout logic to permit the user to alter the lightbox icon to correspond to an actual layout of the lightboxes in a current location during a set-up of the system.

5. The independent display system of claim 4, further comprising:
    a number of preset potential layouts among which the user can choose during said set-up of the system.

6. The independent display system of claim 5, further comprising;
    a programming logic permitting the user to create a customized layout indicator.

7. The independent display system of claim 1, wherein the radiologist selects the lightbox being evaluated on the touch screen by touching the appropriate light box button, to call up said corresponding digitized medical image.

* * * * *